US00PP33089P2

(12) United States Plant Patent
Cain

(10) Patent No.: US PP33,089 P2
(45) Date of Patent: May 25, 2021

(54) GRAPEVINE PLANT NAMED 'IFG FORTY-FIVE'

(50) Latin Name: ***Vitis interspecific* hybrid**
Varietal Denomination: IFG Forty-five

(71) Applicant: David Cain, Bakersfield, CA (US)

(72) Inventor: David Cain, Bakersfield, CA (US)

(73) Assignee: International Fruit Genetics, LLC, Bakersfield, CA (US)

( * ) Notice: Subject to any disclaimer, the term of this patent is extended or adjusted under 35 U.S.C. 154(b) by 0 days.

(21) Appl. No.: 16/602,693

(22) Filed: Nov. 21, 2019

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 6/88; A01H 5/08
See application file for complete search history.

(56) References Cited

U.S. PATENT DOCUMENTS

PP23,315 P2 1/2013 Cain

*Primary Examiner* — Keith O. Robinson

(57) ABSTRACT

This invention is a new and distinct grapevine variety denominated 'IFG Forty-five'. The new grapevine is characterized by producing naturally large, broad ellipsoidal, completely black seedless berries which are firm in texture and ripen early in the growing season. Fruits normally ripen in late July to early August near Delano, Calif.

1 Drawing Sheet

Latin name of the genus and species claimed: *Vitis* interspecific hybrid.

Variety denomination: 'IFG FORTY-FIVE'.

BACKGROUND OF THE INVENTION

The new and distinct Grapevine plant described and claimed herein originated from a hand pollinated cross of 'IFG Eight' (U.S. Plant Pat. No. 23,315) with pollen of the interspecific hybrid 'IFG Forty' (U.S. Plant Pat. No. 31,506) hybridized in May 2012. The abortive seed traces were subsequently embryo cultured and the resulting 148 seedlings were planted in the field in April 2013. The present variety of grapevine was selected as a single plant in August 2014 and was first asexually propagated by hardwood cuttings in December 2014 near Delano, Kern County, Calif. These resulting cuttings produced second generation plants that were planted during April 2015 near Delano, Kern County, Calif. and were observed for four years and found to reproduce true-to-type.

BRIEF SUMMARY OF THE INVENTION

The new grapevine 'IFG Forty-five' is characterized by producing naturally large, broad ellipsoidal, completely black seedless berries which are firm in texture and ripen early in the growing season. Fruits normally ripen in late July to early August near Delano, Calif.

To the inventor's knowledge, the known variety which the new grapevine variety is most similar to is its parent 'IFG Eight' but can be distinguished from the 'IFG Eight' by forming fewer and weaker axillary shoots, having a looser less compact cluster, by having a smaller less noticeable seed trace, by having more abundant cuticular wax, by having firmer berries which are broad ellipsoid in shape as opposed to obtuse ovate shape. 'IFG Forty-five' is more consistently productive and has less tendency to become overly vigorous and unfruitful.

'IFG Forty-five' can be distinguished from its pollen parent the 'IFG Forty' by having a neutral rather than a mild labrusca flavor, by a larger natural berry size, by having a broad ellipsoid berry shape as opposed to the elliptic berry shape of 'IFG Forty'. 'IFG Forty-five' has a stronger, more lignified stem with better berry attachment and has better storage ability than 'IFG Forty'.

'IFG Forty-five is somewhat like 'Summer Royal' (not patented) and can be distinguished from 'Summer Royal' by producing naturally larger berries (about 7.4 grams as opposed to about 5.0 grams for 'Summer Royal'), by having a broader, more desirable cluster shape and thicker and tougher peduncle and pedicle. 'IFG Forty-five' stores better than the 'Summer Royal' variety. 'IFG Forty-five' exhibits very little stem drying, berry shatter or decay when stored for up to eight weeks.

BRIEF DESCRIPTION OF THE DRAWING

The accompanying photographic drawing illustrates in full color 'IFG Forty-five'. The photograph was taken outdoors with indirect lighting. The colors are as nearly true as is reasonably possible in a color representation of this type. The left side of the drawing has a mature leaf. A mature fruit cluster is represented in the center of the drawing along with a typical berry in cross section. A young shoot tip can be seen on the right side of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2016 by The Royal Horticultural Society, London, England.

Throughout this specification, subjective description values conform to those set forth by the UPOV International Union for the Protection of New Varieties of Plants publication 'Grapevine *Vitis* L. Guidelines'.

The descriptive matter which follows pertains to 4-year-old plants of 'IFG Forty-five' grown in the vicinity of Delano, Kern County, Calif. during 2018 and 2019, and is believed to apply to plants of the variety grown under similar conditions of soil and climate elsewhere:

Vine:

*General*.—Vigor — Vigorous. Density of foliage — Medium. Productivity — Productive, producing about 20.3 to 30.4 kg of fruit per vine. Root stock — Own root. Training method — Typically spur pruned leaving 2 bud spurs.

*Trunk*.—Trunk diameter of 4-year-old vines at 30 cm above the soil line — Approximately 5.0 cm. Shape — Moderately stocky. Surface texture — Shaggy texture. Inner bark color — Greyed-orange: 166A. Outer bark color — Brown: N200B.

Shoots:

*Young shoot*.—Form of tip — Wide open. Distribution of anthocyanin coloration of tip — Absent. Intensity of anthocyanin coloration of tip — Absent. Density of prostrate hairs of tip — Sparse. Density of erect hairs on tip — Absent. Color — Yellow-green: 144A.

*Woody shoot* (*mature canes*).—Internode length — Medium: About 9.6 cm. Width at node — About 1.0 cm. Cross section — Circular. Surface — Striate. Main color — The following colors were observed: Brown: 166A and 166B and 166C. Density of erect hairs on nodes — None or very sparse. Density of erect hairs on internodes — None. Axillary shoot vigor at full bloom — Weak, approximately 12.2 cm long.

*Flowering shoot*.—Vigor during flowering — Strong. Attitude during flowering on shoots not tied — Erect. Color — dorsal side of internodes — Yellow-green: 144B, with Greyed-purple stripes: 187C. Color — ventral side of internodes — Yellow-green: 144B, with Greyed-purple stripes on a few shoots: 187C. Color — dorsal side of nodes — Yellow-green: 144B, with Greyed-purple stripes: 187C. Color — ventral side of nodes — Yellow-green: 144B. Density of prostrate hairs on nodes — Very sparse. Density of erect hairs on nodes — None. Density of prostrate hairs on internode — Very sparse. Density of erect hairs on internode — None. Anthocyanin coloration of buds — Absent.

*Tendrils*.—Distribution on the shoot (at full flowering) — Discontinuous. Length of Tendril — Long: About 19.5 cm. Thickness of tendril 2 cm from base — About 1.9 mm. Color — Yellow-green: 144C. Form — Mixture of bifurcated and trifurcated. Number of consecutive tendrils — 2.

Leaves:

*Young leaves*.—Color of upper surface of first four distal unfolded leaves — Yellow-green: 144A. Color of lower surface of young leaves — Yellow-green: 144A. Average intensity of anthocyanin coloration of six distal leaves prior to flowering — Absent. Density of prostrate hairs between veins (lower surface) — Very sparse. Density of prostrate hairs on veins (lower surface) — Very sparse. Density of erect hairs between veins (lower surface) — Absent. Density of erect hairs on veins (lower surface) — Absent to very sparse.

*Mature leaves* (*opposite first cluster*).—Average length — About 11.0 cm. Average width — About 12.2 cm. Mature leaf size — Medium. Shape of blade — Wedge-shaped. Number of lobes — 5. Blade venation — Palmate. Anthocyanin coloration of main veins on upper side of blade — Medium. Mature leaf profile — Undulate. Blistering surface of blade upper surface — Absent to very weak. Leaf blade tip — In the plane of the leaf. Leaf apex — Broadly acute. Leaf margin — Serrate. Undulation of margin — Slight. Undulation of blade between main and lateral veins — Slight undulation over entire area. Shape of teeth — Mixture of both sides straight and both sides convex. Length of teeth — Short: Approximately 4.3 mm. Width of teeth — Medium: Approximately 7.3 mm. Ratio length/width of teeth — Medium: Approximately 0.6. Shape of upper lateral sinuses — Lobes strongly overlapping. Depth of upper lateral sinuses — Medium. General shape petiole sinus — Wide open to very wide open. Shape of base of upper leaf sinuses — U-shaped. Tooth at petiole sinus — Absent. Density of prostrate hairs between veins on lower surface of blade — Very sparse. Density of erect hairs between veins on lower surface of blade — Absent. Density of prostrate hairs on main veins on lower surface of blade — Very sparse. Density of erect hairs on main veins on lower surface of blade — Very sparse. Density of prostrate hairs on main veins on upper surface of blade — Very sparse. Density of erect hairs on main veins on upper surface of blade — None. Autumn coloration of leaves — Leaves can be a single color or combination of colors, in a mottled pattern or on the edges of the leaves. The following colors were observed: Greyed-purple: 184A and 185A and Yellow-orange: 22A and Yellow: 11A.

*Upper surface*.—Color — Green: 137A. Anthocyanin coloration of main veins (lower surface) — Strong: Greyed-purple: 187C. Color of main veins — Yellow-green: 146C. Surface appearance — Semi-glossy. Blistering surface of blade — Weak.

*Lower surface*.—Color — Yellow-green: 146A. Anthocyanin coloration of main veins (lower surface) — Medium: Greyed-purple: 187C. Color of main veins — Yellow-green: 145C. Glossiness — Medium. Surface texture — Smooth. Surface appearance — Semi-glossy.

*Petiole*.—Length — About 11.5 cm. Diameter of petiole 2 cm from blade — About 2.5 mm. Petiole color — The following colors were observed: Yellow-green: 144D and Greyed-purple: 187C. Length of petiole compared to middle vein — Equal to slightly longer. Density of prostrate hairs on petiole — None to very sparse. Density of erect hairs on petiole — None.

*Buds*.—Bud fruitfulness — Basal: mostly fruitful. Position of first fruitful shoot on previous season cane — $1^{st}$ node. Dormant bud length — About 6.0 mm. Dormant bud width in the proximal/distal plane — About 5.2 mm. Dormant bud color — Greyed-orange: 166A. Time of bud burst — About Mar. 21, 2019.

Flowers:

*General*.—Flower sex — Hermaphrodite. Length of single flower, unopened — About 2.8 mm. Width of single flower — Unopened: About 2.2 mm. Opened: About 6.8 mm. Stamen length — About 3.7 mm. Stamen count — 6. Pollen color — Yellow: 10C. Pistil length — About 2.8 mm. Pistil color — Yellow-green: 145A. Length of first inflorescence — Medium: About 18.0 cm long by 9.0 cm wide. Position of first flowering and fruiting node — $5^{th}$ node (current season growth). Number of inflorescence per flowering shoot — 1.1 to 2: About 2.0. Time of bloom — Early as compared with similar varieties in the growing area of Delano, Calif. Date of full bloom — About May 6, 2019.

Fruit:

*General*.—Ripening period — Early to mid-season: Approximately Jul. 20, 2018. Use — Fresh market. Keeping quality — Excellent, remains commercially acceptable when stored up to 8 weeks at 0° C. and high relative humidity. Refractometer test — Soluble solids: About 19.2 Brix. Brix/acid — About 25.9. Titratable acidity — About 0.74. Juice pH — About 3.7. Juice color — Greyed-orange: 177C.

*Cluster*.—Mature cluster length (peduncle excluded) — About 23.2 cm. Mature cluster width — About 16.4 cm. Mature cluster weight — About 677 g. Bunch density — Loose: single berries loosely spaced, some pedicels visible. Number of berries — About 117. Form — Conical.

*Peduncle*.—Lignification of peduncle — Weak. Diameter of peduncle — About 0.6 cm. Length of peduncle — Short: Approximately 2.7 cm. Color of peduncle — Yellow-green: 144C.

*Berry*.—Uniformity of size — Uniform. Single berry weight — About 7.4 g natural; to about 7.5 g when treated with gibberellic acid. Shape — Broad ellipsoid. Seeds — Mixture of absent to a few small rudimentary seed traces. Cross section — Circular. Berry dimensions — Longitudinal axis: About 2.6 cm. Horizontal axis: About 2.2 cm. Pedicel length — About 8.3 mm. Pedicel width — About 1.8 mm. Pedicel color — Yellow-green: 144C. Berry firmness — Firm. Particular flavor — Neutral. Bloom (cuticular wax) — Strong. Berry separation from pedicel — Moderate. Skin color (without bloom) — Greyed-purple: N186A. Flesh color — Greyed-green: 193C.

*Skin*.—Thickness — Medium. Skin toughness — Not notable when chewing. Reticulation — Absent. Tenacity — Tenacious to flesh.

What is claimed:

1. A new and distinct variety of grapevine plant as herein illustrated and described.

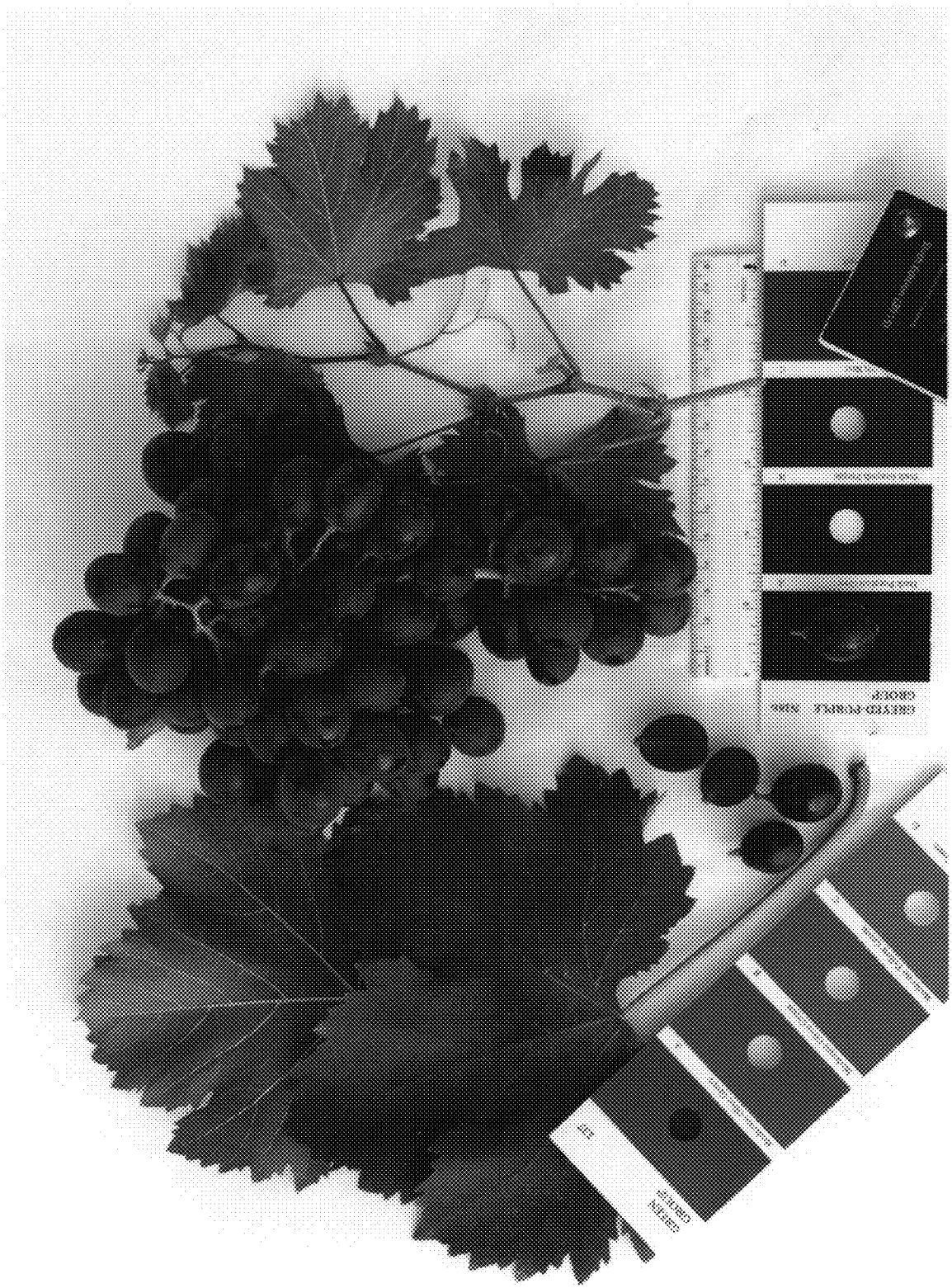

* * * * *